United States Patent

Zeun et al.

[11] Patent Number: 5,554,619
[45] Date of Patent: Sep. 10, 1996

[54] MICROBICIDES

[75] Inventors: Ronald Zeun, Neuenburg, Germany; René Zurflüh, Bülach, Switzerland

[73] Assignee: Ciba-Geigy Corporation, Tarrytown, N.Y.

[21] Appl. No.: 424,683

[22] Filed: Apr. 18, 1995

Related U.S. Application Data

[62] Division of Ser. No. 268,090, Jun. 28, 1994, Pat. No. 5,436,248.

[30] Foreign Application Priority Data

Jul. 2, 1993 [CH] Switzerland .............. 2007/93
Jul. 16, 1993 [CH] Switzerland .............. 2155/93

[51] Int. Cl.⁶ .............. A01N 37/12; A01N 37/44; A01N 43/54
[52] U.S. Cl. .............. 514/275; 514/539
[58] Field of Search .............. 514/225, 539

[56] References Cited

U.S. PATENT DOCUMENTS

| | | | |
|---|---|---|---|
| 4,829,085 | 5/1989 | Wenderoth et al. | 514/522 |
| 5,145,856 | 9/1992 | Clough et al. | 514/274 |
| 5,145,980 | 9/1992 | Wenderoth et al. | 560/35 |
| 5,153,200 | 10/1992 | Hubele | 514/275 |
| 5,242,920 | 9/1993 | Sauter et al. | 514/239 |
| 5,260,326 | 11/1993 | Sauter et al. | 514/383 |

FOREIGN PATENT DOCUMENTS

| | | |
|---|---|---|
| 0524496 | 1/1993 | European Pat. Off. |
| 0531837 | 3/1993 | European Pat. Off. |
| 2267644 | 12/1993 | United Kingdom |

OTHER PUBLICATIONS

Research Disclosure, No. 346, Feb. 1993, Emsworth, GB.

*Primary Examiner*—Allen J. Robinson
*Attorney, Agent, or Firm*—Edward McC. Roberts

[57] ABSTRACT

Microbicidal composition for use in plants, having a synergistic action and comprising at least two active ingredient components, in which component I is a compound selected from the group of the compounds

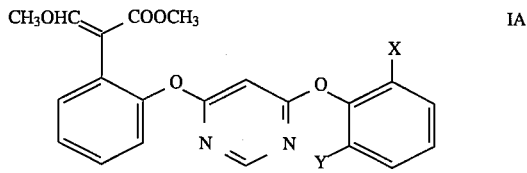

in which:

X is hydrogen, halogen, $C_1$–$C_4$alkyl, $C_1$–$C_4$alkoxy, trifluoromethyl, cyano, thiocarbamoyl or nitro, and Y is hydrogen or fluorine;

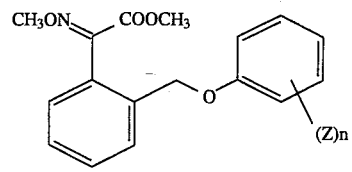

in which:

Z radicals are identical or different and are halogen, cyano, nitro, $C_1$–$C_4$alkyl, $C_1$–$C_4$alkoxy, trifluoromethyl, phenyl, phenoxy or benzyl, these aromatic groups being unsubstituted or not more than trisubstituted by identical or different substituents from the series comprising halogen, cyano, nitro, $C_1$–$C_4$alkyl, $C_1$–$C_4$alkoxy or trifluoromethyl, and n is 0 to 3; and

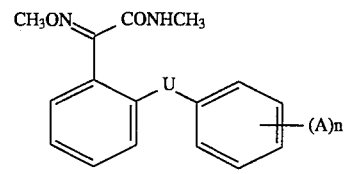

in which:

U is oxygen or the group —$CH_2O$—,

A radicals are identical or different and are halogen, $C_1$–$C_4$alkyl, $C_1$–$C_4$alkoxy or trifluoromethyl, and n is 0 to 3;
and in which component II is the 2-anilinopyrimidine of the formula II

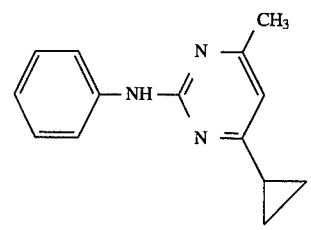

4-cyclopropyl-6-methyl-N-phenyl-2-pyrimidineamine or a salt or a metal complex thereof.

7 Claims, No Drawings

MICROBICIDES

This is a division of application No. 08/268,090, filed Jun. 28, 1994, now U.S. Pat. No. 5,436,248, issued Jul. 25, 1995.

The present invention relates to novel microbicidal two-component mixtures which have a synergistically enhanced action and to methods for the use of such mixtures in crop protection.

Component I is a strobilurin analogue compound of the formula IA

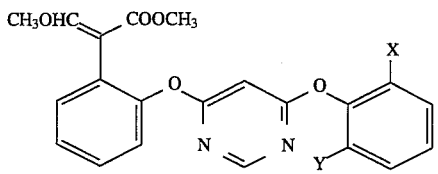

in which:

X is hydrogen, halogen, $C_1$-$C_4$alkyl, $C_1$-$C_4$alkoxy, trifluoromethyl, cyano, thiocarbamoyl or nitro, and Y is hydrogen or fluorine; (reference: EP-A-382 375);

or of the formula IB

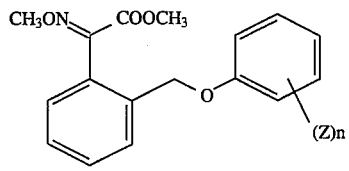

in which:

Z radicals are identical or different and are halogen, cyano, nitro, $C_1$-$C_4$alkyl, $C_1$-$C_4$-alkoxy, trifluoromethyl, phenyl, phenoxy or benzyl, these aromatic groups being unsubstituted or not more than trisubstituted by identical or different substituents from the series comprising halogen, cyano, nitro, $C_1$-$C_4$alkyl, $C_1$-$C_4$alkoxy or trifluoromethyl, and n is 0 to 3; (references: EP-A-253 213 and EP-A-400 417);

or of the formula IC

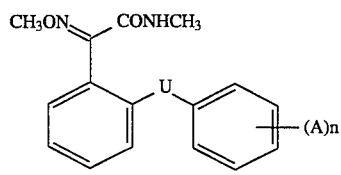

in which:

U is oxygen or the group —$CH_2O$—,

A radicals are identical or different and are halogen, $C_1$-$C_4$alkyl, $C_1$-$C_4$alkoxy or trifluoromethyl, and n is 0 to 3. (Reference: EP-A-398 692).

Component II is the 2-anilinopyrimidine of the formula II

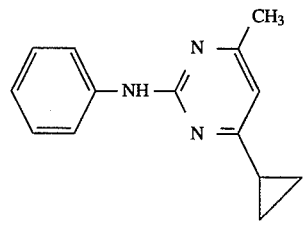

4-cyclopropyl-6-methyl-N-phenyl-2-pyrimidineamine or a salt or a metal complex thereof (reference: EP-A-310 550).

The invention also relates to salts of compounds I and II. These salts are formed, for example, with mineral acids, for example sulfuric acid, a phosphoric acid or a hydrohalic acid, with organic carboxylic acids, for example acetic acid, oxalic acid, malonic acid, maleic acid, fumaric acid or phthalic acid, with hydroxycarboxylic acids, for example ascorbic acid, lactic acid, malic acid, tartaric acid or citric acid, or with benzoic acid, or with organic sulfonic acids, for example methane- or p-toluenesulfonic acid. Preferred within the scope of the invention are agrochemically advantageous salts.

The term salts also includes metal complexes of basic components I and II. These complexes can relate either to one component only or else to both components independently, as desired. It is also possible to prepare metal complexes which combine the two active ingredients I and II to give a mixed complex.

Metal complexes are composed of the organic molecule on which they are based and on an inorganic or organic metal salt, for example the halides, nitrates, sulfates, phosphates, acetates, trifluoroacetates, trichloroacetates, propionates, tartrates, sulfonates, salicylates, benzoates and the like of the elements of the second Main Group, such as calcium and magnesium, and of the third and fourth Main Group, such as aluminium, tin or lead, and of the first to eighth Sub-group, such as chromium, manganese, iron, cobalt, nickel, copper, zinc and the like. The Sub-group elements of the 4th Period are preferred. The metals can have the various valencies which they can assume. The metal complexes can be mononuclear or polynuclear, i.e. they can contain one or more organic moieties as ligands.

Halogen is fluorine, chlorine, bromine and iodine; fluorine, chlorine and bromine are preferred.

The alkyl moiety in the $C_1$-$C_4$ alkyl groups and $C_1$-$C_4$alkoxy groups is methyl, ethyl, propyl, isopropyl, butyl, isobutyl, sec-butyl and tert-butyl; methyl and methoxy are preferred.

Thiocarbamoyl is the radical —CS—$NH_2$.

Due to their aliphatic or imino double bond, the compounds of the formulae IA, IB and IC exist in the E and Z forms. Furthermore, atropisomers can occur. The formulae IA, IB and IC are intended to embrace all isomers which are possible and their mixtures.

Preferred are the compounds IA, IB and IC in the E form.

Preferred mixtures are those in which, in compound IA,

X is hydrogen, chlorine, methyl, methoxy, trifluoromethyl or cyano, and

Y is hydrogen or fluorine;

very particularly preferred is methyl 2-{ 2-[6-(2-cyanophenoxy)pyrimidin- 4-yloxy]phenyl}-3-methoxyacrylate, and, in particular, the E isomer thereof, which will be termed IA* here and in what follows.

Other mixtures which are preferred are those in which, in compound IB,

Z is chlorine, methyl, methoxy, trifluoromethyl or cyano, and n is 0, 1 or 2;

very particularly preferred is methyl 2-methoximino-2-[α-(o-tolyloxy)-o-tolyl]acetate, and in particular the E isomer thereof, which will be termed IB* here and in what follows.

In compound IC in another group of preferred mixtures,

U is oxygen or the group —$CH_2O$—,

A is halogen, methyl, methoxy or trifluoromethyl, and n is 0, 1 or 2;

very particularly preferred are the compounds N-methyl-2-(2-phenoxyphenyl)-2-methoxyiminoacetamide and N-methyl-2-[2-(2,5-dimethylphenoxymethyl)-phenyl]-2-methoxyiminoacetamide, and of these two in particular the E isomers, which will be termed IC-1* and IC-2* here and in what follows.

Other agrochemical active ingredients, such as insecticides, acaricides, nematicides, herbicides, growth regulators and fertilizers but, in particular, other microbicides, can also be added to the mixture of active ingredients according to the invention.

Surprisingly, it has now emerged that mixtures of components I and II not only display an additive effect with regard to their fungicidal action, but a clear synergistically enhanced effect.

The mixture according to the invention has the particular advantage of preventing the development of resistance in plant diseases, since the microbicidal action of the two components I and II is based on different biochemical mechanisms. While strobilurin analogues of type I inhibit the mitochondrial respiration by blocking the electron transfer on the cytochrome bc1 complex, the activity of the pyrimidineamine II is based on an inhibition of amino acid synthesis.

The present invention therefore represents an essential enlargement of the art.

Another object of the present invention, in addition to the two-component mixture, is a method of controlling fungi, which comprises treating the location which is infested with or endangered by fungi in any desired sequence or simultaneously with a) an active ingredient of the formula I or a salt thereof, and b) the active ingredient of the formula II or a salt thereof, it also being possible for the salt to be selected in such a manner that both active ingredients are bonded to an acid radical or, in the case of a metal complex, to a central metal cation.

Favourable ratios of the two active ingredients in the mixture are I:II= 1:20 to 10:1, preferably I:II= 1:6 to 3:1.

In many cases, advantageous mixtures are those in which the ratio of the pure active ingredients in the mixture is I:II= 1:3 to 1:1, for example 1:2, 2:3, 2:5, 3:4.

The mixtures of the active ingredients I+ II according to the invention have highly advantageous curative, preventive and systemic fungitidal properties for protecting plants. Using the present mixtures of active ingredients, it is possible to contain or destroy the microorganisms which occur on plants or parts of plants (fruits, flowers, foliage, stalks, tubers, roots) of a range of crops of useful plants, and even parts of plants which are produced later remain unharmed by such microorganisms. They can also be used as seed-dressing products for the treatment of plant propagation material, in particular seeds (fruits, tubers, kernels) and plant cuttings (for example rice) as a protection against fungal infections and against soil-borne phytopathogenic fungi. The mixtures of active ingredients according to the invention are distinguished by the fact that they are particularly well tolerated by plants and that they are environmentally friendly.

The mixtures of active ingredients are effective against the phytopathogenic fungi of the following classes: Ascomycetes (for example Venturia, Podosphaera, Erysiphe, Monilinia, Uncinula); Basidiomycetes (for example Hemileia, Rhizoctonia, Puccinia); Fungi imperfecti (for example Botrytis, Helminthosporium, Rhynchosporium, Fusarium, Septoria, Cercospora, Alternaria, Pyricularia and *Pseudocercosporella herpotrichoides*); and Oomycetes (for example Phytophthora, Peronospora, Bremia, Pythium, Plasmopara).

Target crops for the fields of indication disclosed herein are, within the scope of the present invention, for example the following types of plants: cereals (wheat, triticale, barley, rye, oats, rice, sorghum and related species); beet (sugar and fodder beet); pome fruit, stone fruit and soft fruit (apples, pears, plums, peaches, almonds, cherries, strawberries, raspberries and blackberries); leguminous plants (beans, lentils, peas, soya beans); oil crops (oilseed rape, mustard, poppies, olives, sunflowers, coconut, castor, cocoa, groundnuts); cucurbits (pumpkin, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell peppers); the laurel family (avocado, Cinnamonum, camphor), or plants such as maize, tobacco, nuts, coffee, sugar cane, tea, grapevines, hops, the banana family, latex plants and ornamentals (flowers, shrubs, deciduous trees and coniferous trees). This enumeration is no limitation.

The mixtures of active ingredients according to the invention are particularly effective as fungitides in cereals, in potatoes, in vines and in fruit growing.

The mixtures of active ingredients of the formulae I and II are conventionally used in the form of compositions. The active ingredients of the formula I and the active ingredient of the formula II can be applied to the area or plant to be treated simultaneously, or else in succession on the same day, if appropriate together with other carriers conventionally used in the art of formulation, surfactants or other additives which facilitate application.

Suitable carriers and additives can be solid or liquid and are those substances advantageously used in the art of formulation, for example natural or regenerated mineral substances, solvents, dispersants, wetting agents, adhesives, thickeners, binders or fertilizers.

A preferred process for applying a mixture of active ingredients which contains at least one of these active ingredients I and II is applying it to the aerial parts of the plants, especially to the foliage foliar application). Number and rate of applications will depend on the biological and climatic environment of the pathogen. Alternatively, the active ingredients can reach the plant via the soil and the root system (systemic action), by drenching the locus of the plant with a liquid preparation or incorporating the substances in solid form into the soil, for example in the form of granules (soil application). For the treatment of seed, the compounds of the formulae I and II can be applied, for example, to seed kernels (coating) either by soaking the tubers or kernels in succession in a liquid preparation of an active ingredient or by coating them with a moist or dry preparation which is already a combination. Moreover, specific cases allow other methods of application to plants, for example the targeted treatment of the buds or the fruiting organs.

The compounds of the combination are employed as pure active ingredients or, preferably, together with the auxiliaries conventionally used in the art of formulation, and they are therefore processed in a known manner to give, for example, emulsion concentrates, spreadable pastes, directly sprayable or dilutable solutions, dilute emulsions, wettable powders, soluble powders, dusts, granules, or encapsulations, for example in polymeric substances. The methods of application, such as spraying, atomizing, dusting, scattering, painting on or pouring, and the nature of the compositions are selected to suit intended aims and the prevailing circumstances. Advantageous application rates of the mixture of active ingredients are generally 5 g to 1000 g of A.I./ha, preferably 50 g to 700 g of A.I./ha, particularly preferably 60 g to 500 g of A.I./ha. For the treatment of seed, the rates of application are 0.5 g-S800 g, preferably 5 g-100 g, of A.I. per 100 kg of seed.

The formulations are produced in the known manner, for example by intimately mixing and/or grinding the active ingredients with extenders, for example with solvents, solid carders and, if desired, surface-active compounds (surfactants).

The following are possible as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and epoxidized or unepoxidized vegetable oils, such as epoxidized coconut oil or soya oil; or water.

Solid carriers which are used for example for dusts and dispersible powders, are, as a rule, ground natural minerals, such as calcite, talc, kaolin, montmorillonite or attapulgite. To improve the physical properties, it is also possible to add highly disperse silica or highly disperse absorptive polymers. Possible particulate, adsorptive carriers for granules are either porous types, for example pumice, brick grit, sepiolite or bentonite, or non-sorptive carrier materials, for example calcite or sand. Moreover, a large number of pregranulated materials of inorganic or organic nature can be used such as, in particular, dolomite or comminuted plant residues.

Suitable surface-active compounds are non-ionic, cationic and/or anionic surfactants having good emulsifying, dispersing and wetting properties, depending on the nature of the active ingredients of the formulae I and II to be formulated. Surfactants are also to be understood as meaning mixtures of surfactants.

The surfactants conventionally used in the art of formulation are described, inter alia, in the following publications:

"Mc Cutcheon's Detergents and Emulsifiers Annual" MC Publishing Corp., Glen Rock, N.J., 1988.

M. and J. Ash, "Encyclopedia of Surfactants", Vol. I–III, Chemical Publishing Co., N.Y., 1980–1981.

Particularly advantageous adjuvants which favour application are, furthermore, natural or synthetic phospholipids from the series comprising the cephalins and the lecithins, for example phosphatidylethanolamine, phosphatidylserine, phosphatidylglycerine, lysolecithin.

As a rule, the agochemical preparations comprise 0.1 to 99%, in particular 0.1 to 95%, of active ingredients of the formulae I and II, 99.9 to 1%, in particular 99.9 to 5%, of a solid or liquid additive, and 0 to 25%, in particular 0.1 to 25%, of a surfactant.

While concentrated compositions are more preferred as commercially available goods, the end user will, as a rule, use dilute compositions.

Such (agro)chemical compositions are part of the present invention.

The examples which follow are intended to illustrate the invention, "active ingredient" being understood as meaning a mixture of compound I and compound II in a specific ratio.

Formulation Examples

| Wettable powders | a) | b) | c) |
|---|---|---|---|
| Active ingredient [I:II = 4:1 (a), 1:1(b), 1:2(c)] | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives and ground thoroughly in a suitable mill. This gives wettable powders which can be diluted with water to give suspensions of any desired concentration.

| Emulsion concentrate | |
|---|---|
| Active ingredient (I:II = 2:3) | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution which can be employed in crop protection can be prepared from this concentrate by diluting it with water.

| Dusts | a) | b) | c) |
|---|---|---|---|
| Active ingredient [I:II = 1:4 (a); 1:5 (b) and 1:1 (c)] | 5% | 6% | 4% |
| Talc | 95% | — | — |
| Kaolin | — | 94% | — |
| Ground minerals | — | — | 96% |

Ready-to-use dusts are obtained by mixing the active ingredient with the carrier and grinding the mixture on a suitable mill. Such powders can also be used for dry-dressing seed.

| Extruder granules | |
|---|---|
| Active ingredient (I:II = 3:4) | 14% |
| Sodium ligninsulfonate | 2% |
| Carboxymethylcellulose | 1% |
| Kaolin | 83% |

The active ingredient is mixed with the additives and ground, and the product is moistened with water. This mixture is extruded and subsequently dried in a stream of air.

| Coated granules | |
|---|---|
| Active ingredient (I:II = 3:5) | 8% |
| Polyethylene glycol (MW 200) | 3% |
| Kaolin | 89% |

(MW = molecular weight)

In a mixer, the kaolin, which has been moistened with polyethylene glycol, is coated uniformly with the finely ground active ingredient. In this manner, dust-free coated granules are obtained.

| Suspension concentrate | |
|---|---|
| Active ingredient (I:II = 3:7) | 40% |
| Propylene glycol | 10% |
| Nonylphenol polyethylene | 6% |

-continued

| | |
|---|---|
| glycol ether (15 mol of ethylene oxide) | |
| Sodium ligninsulfonate | 10% |
| Carboxymethylcellulose | 1% |
| Silicone oil (in the form of a 75% aqueous emulsion) | 1% |
| Water | 32% |

The finely ground active ingredient is mixed intimately with the additives. This gives a suspension concentrate from which suspensions of any desired dilution can be prepared by diluting it with water. Such dilutions can be used for protecting live plants and plant propagation material against infestation by microorganisms by spraying, sprinkling or immersing it.

Biological Examples

The tests which follow were carried out using mixtures of the individual compounds IA*, IB*, IC-1* or IC-2* and II which have been mentioned further above. Their improved effectiveness in the biological tests which follow and in further biological tests are largely representative of the improved activities found with other representatives of the formula I.

A synergistic effect in fungicides exists whenever the fungicidal activity of the combination of the active ingredients exceeds the total of the activities of the active ingredients when applied individually.

The activity to be expected E for a given combination of active ingredients, for example two fungicides, is described by the so-called COLBY formula and can be calculated as follows (COLBY, S.R. "Calculating synergistic and antagonistic responses of herbicide combination", Weeds, Vol. 15, pages 20–22; 1967): if ppm= milligram of active ingredient (= A.I.) per liter spray mixture X= % activity by fungicide I when using p ppm of active ingredient Y= % activity by fungicide II when using q ppm of active ingredient E= expected activity of fungicities I+ II when using p+q ppm of active ingredient (additive effect),
then Colby's formula reads $$E = X + Y - \frac{X \cdot Y}{100}.$$

If the actually observed activity (O) exceeds the expected activity (E), then the combination has a superadditive activity, i.e. there is a synergistic effect.

O/E= synergistic factor (SF).

In the examples which follow, let the infestation of the untreated plants be 100%, which corresponds to an activity of 0%.

EXAMPLE 1: Activity against Botrytis cinerea in apples

Artificially damaged apples are treated by dropwise application of a spray mixture (30 microliters of the active ingredient, or of the combination of the active ingredients) to the site of the damage. The treated fruits are subsequently inoculated with a spore suspension of the fungus and incubated for one week at approximately 20° C. at high atmospheric humidity. The fungicidal activity of the test substance is derived from the number and size of the sites of damage which show incidents of rot. The following results are obtained:

TABLE 1a

Active ingredient I: 1A* = E-methyl 2-{2-[6-(2-cyanophenoxy)pyrimidin-4-yloxyl]phenyl}-3-methoxyacrylate.

| | mg of A.I per litre | | | % Activity | | |
|---|---|---|---|---|---|---|
| Exp. No. | IA* | II | I:II | found O | calculated E | SF O/E |
| 0 | — | — | | 0 (control) | | |
| 1 | 2 | — | | 50 | | |
| 2 | 6 | — | | 75 | | |
| 3 | — | 0.6 | | 0 | | |
| 4 | — | 2 | | 55 | | |
| 5 | 2 | 0.6 | 3:1 | 90 | 50 | 1.8 |
| 6 | 6 | 0.6 | 10:1 | 90 | 75 | 1.2 |
| 7 | 2 | 2 | 1:1 | 98 | 78 | 1.3 |

TABLE 1b

Active ingredient I: 1B* = E-methyl 2-methoximino-2-[α-(o-tolyloxy)-o-tolyl]acetate

| | mg of A.I per litre | | | % Activity | | |
|---|---|---|---|---|---|---|
| Exp. No. | IB* | II | I:II | found O | calculated E | SF O/E |
| 0 | — | — | | 0 (control) | | |
| 1 | 2 | — | | 35 | | |
| 2 | 6 | — | | 35 | | |
| 3 | — | 0.6 | | 0 | | |
| 4 | — | 2 | | 55 | | |
| 5 | 2 | 0.6 | 3:1 | 95 | 35 | 2.7 |
| 6 | 2 | 2 | 1:1 | 90 | 71 | 1.2 |
| 7 | 6 | 0.6 | 10:1 | 95 | 35 | 2.7 |

EXAMPLE 2: Activity against Pyrenophora teres in barley

Barley plants which are 6 days old are sprayed to drip point using a spray mixture prepared with the formulated active ingredient, or combination of active ingredients. After 2 days, the plants are inoculated with a spore suspension of Pyrenophora teres and incubated in the greenhouse at 21° C. and an atmospheric humidity of 90–100%. After one week, the fungus infestation is assessed. The following results are obtained:

TABLE 2a

Active ingredient I: 1A* = E-methyl 2-{2-[6-(2-cyanophenoxy)pyrimidin-4-yloxyl]phenyl}-3-methoxyacrylate.

| | mg of A.I per litre | | | % Activity | | |
|---|---|---|---|---|---|---|
| Exp. No. | IA* | II | I:II | found O | calculated E | SF O/E |
| 0 | — | — | | 0 (control) | | |
| 1 | 0.2 | — | | 50 | | |
| 2 | — | 2 | | 0 | | |

TABLE 2a-continued

Active ingredient I: 1A* = E-methyl 2-{2-[6-(2-cyanophenoxy)pyrimidin-4-yloxyl]phenyl}-3-methoxyacrylate.

| Exp. No. | mg of A.I per litre | | | % Activity | | SF |
|---|---|---|---|---|---|---|
| | IA* | II | I:II | found O | calculated E | O/E |
| 3 | 0.2 | 2 | 1:10 | 75 | 50 | 1.5 |

TABLE 2b

Active ingredient I: 1B* = E-methyl 2-methoximino-2-[α-(o-tolyloxy)-o-tolyl]acetate

| Exp. No. | mg of A.I per litre | | | % Activity | | SF |
|---|---|---|---|---|---|---|
| | IB* | II | I:II | found O | calculated E | O/E |
| 0 | — | — | | 0 (control) | | |
| 1 | 0.6 | — | | 0 | | |
| 2 | 2 | — | | 35 | | |
| 3 | — | 2 | | 0 | | |
| 4 | — | 6 | | 35 | | |
| 5 | 0.6 | 2 | 1:3 | 65 | 0 | * |
| 6 | 0.6 | 6 | 1:10 | 50 | 35 | 1.4 |
| 7 | 2 | 6 | 1:3 | 65 | 58 | 1.1 |

*Synergy factor SF not calculable.

EXAMPLE 3: Activity against *Pseudocercosporella herpotrichoides* in wheat

Wheat plants which are 10 days old are sprayed to drip point with a spray mixture prepared with the formulated active ingredient, or the combination of active ingredients. After 48 hours, the treated plants are infected with a conidia suspension of the fungus, the treated plants are subsequently incubated for 2 days at a relative atmospheric humidity of 90–100% and at 20° C. and placed in a controlled-environment cabinet at 12° C. for a further 8 weeks. 9 weeks after the infection, the fungus infestation is assessed.

A synergistically enhanced fungicidal activity is found at various ratios of components I+II in the mixture.

EXAMPLE 4: Activity against *Erysiphe graminis* in winter wheat

Approximately 20 winter wheat plants of the variety "Bernina" are grown in the greenhouse in pots of diameter 16 cm at 20° C. and a relative atmospheric humidity of 60% during a 12-hour-day and at 16° C. and a relative atmospheric humidity of 80% during the night. At the beginning of tillering (EC 21 ), the plants are inoculated with an isolated preparation of *Erysiphe graminis* f.sp. tritici.

3 days after the inoculation, the individual active ingredient, or the mixture of the active ingredients, is applied in the form of an aqueous suspension under field conditions using a spray boom and an application rate of 500 l of water/ha. 4 and 11 days after the application, the change in infestation on the leaf area present at the time of inoculation is determined (evaluation of the primary infestation). 3 replications are carried out for each test.

A synergistically enhanced fungicidal activity is found at various ratios of components I+II in the mixture.

EXAMPLE 5: Activity against *Alternaria solani*

The Alternaria strain is grown for one week on 20% V8-agar at 22° C. in the dark.

To test the fungicidal activity, a range of concentrations of active ingredient is incorporated into the V8-agar, onto the surface of which in the Petri dish *A. solani* is inoculated. 4 replications are carried out for each concentration. After 7 days, the radial growth of the fungus or its inhibition is determined.

A synergistically enhanced fungitidal activity is found at various ratios of components I+II in the mixture.

What is claimed is:

1. A microbicidal composition for use in plants, comprising synergistic fungicidally effective amounts of at least two active ingredient components, wherein component I is a compound of formula IB

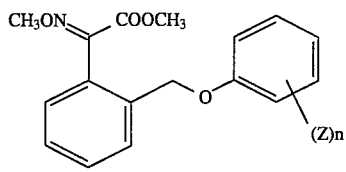

in which:

Z is methyl and n is 0, 1 or 2; and component II is the 2-anilinopyrimidine of formula II

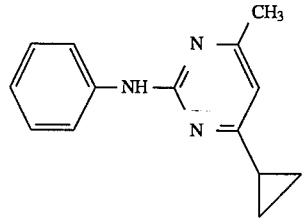

4-cyclopropyl-6-methyl-N-phenyl-2-pyrimidineamine, or a salt or a metal complex thereof; together with an inert carrier;

wherein the weight ratio of the active ingredients I and II is in the range of 1:10 to 10:1.

2. The composition of claim 1, wherein the compound of formula IB has the E form.

3. The composition according to claim 1, wherein the compound IB is methyl (E)-2-methoximino-2-[α-(o-tolyloxy)-o-tolyl]acetate.

4. The composition according to claim 1, wherein the ratio by weight of I:II is 1:6 to 3:1.

5. A method of controlling and preventing plant diseases, which comprises treating a plant or a plant locus which is infested with or endangered by fungi in either sequence or simultaneously with a synergistic fungicidally effective amount of component I and component II according to claim 1.

6. The method according to claim 5, wherein plant propagation material is treated.

7. A plant propagation material treated according to claim 6.

* * * * *